United States Patent
Schuijers et al.

(10) Patent No.: US 11,237,669 B2
(45) Date of Patent: Feb. 1, 2022

(54) METHOD AND APPARATUS FOR IMPROVING THE MEASUREMENT OF THE TIMING OF TOUCHES OF A TOUCH SCREEN

(71) Applicant: KONINKLIJKE PHILIPS N.V., Eindhoven (NL)

(72) Inventors: Erik Gosuinus Petrus Schuijers, Breda (NL); Bjorn Nicolaas Servatius Vlaskamp, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/639,767

(22) PCT Filed: Sep. 5, 2018

(86) PCT No.: PCT/EP2018/073843
§ 371 (c)(1),
(2) Date: Feb. 18, 2020

(87) PCT Pub. No.: WO2019/048462
PCT Pub. Date: Mar. 14, 2019

(65) Prior Publication Data
US 2020/0210042 A1   Jul. 2, 2020

(30) Foreign Application Priority Data
Sep. 7, 2017 (EP) .................................. 17189896

(51) Int. Cl.
*G06F 3/041* (2006.01)
*G06F 3/042* (2006.01)
(Continued)

(52) U.S. Cl.
CPC .......... *G06F 3/04166* (2019.05); *G06F 3/042* (2013.01); *G06F 9/451* (2018.02); *G16H 20/70* (2018.01)

(58) Field of Classification Search
CPC ...... G06F 3/04166; G06F 3/042; G06F 9/451; G16H 20/70
(Continued)

(56) References Cited

U.S. PATENT DOCUMENTS

| 8,521,439 B2 | 8/2013 | Mollicone et al. |
| 8,794,976 B2 | 8/2014 | Kan et al. |

(Continued)

FOREIGN PATENT DOCUMENTS

EP     2674845 A1   12/2013

OTHER PUBLICATIONS

Dinges, D. et al., "Microcomputer analyses of performance on a portable, simple visual RT task during sustained operations." Behavior Research Methods, Instruments, & Computers, 17, 652-655, (1985).

(Continued)

*Primary Examiner* — Mark Edwards

(57) ABSTRACT

The invention relates to a method and apparatus for improving the measurement of the timing of touches of a touch screen. In an embodiment a method of determining a time at which a user touched a touch screen of an electronic device comprises obtaining (101) a touch signal generated by the touch screen for a first time period, the touch signal indicating when the user touched the touch screen during the first time period; obtaining (103) a sensor signal generated by a first sensor for at least the first time period, the sensor signal comprising a first signal component corresponding to a measurement by the first sensor of the user making contact with the touch screen; using (105) the touch signal to (Continued)

identify a time window in the sensor signal containing the first signal component; and processing (107) the windowed sensor signal to determine the timing of the first signal component in the sensor signal.

16 Claims, 6 Drawing Sheets

(51) Int. Cl.
*G16H 20/70* (2018.01)
*G06F 9/451* (2018.01)

(58) Field of Classification Search
USPC .......................................................... 345/175
See application file for complete search history.

(56) References Cited

U.S. PATENT DOCUMENTS

| 9,002,671 | B2 | 4/2015 | Kan et al. |
| 10,254,785 | B2 | 4/2019 | Devilbiss et al. |
| 2013/0113751 | A1* | 5/2013 | Uzelac .................... G06F 3/041 |
| | | | 345/174 |
| 2014/0324422 | A1* | 10/2014 | Winarski ............ H04L 65/4076 |
| | | | 704/235 |
| 2015/0097803 | A1* | 4/2015 | Leigh ..................... G06F 3/041 |
| | | | 345/174 |
| 2017/0177023 | A1* | 6/2017 | Simon .................... G16H 50/20 |

OTHER PUBLICATIONS

Ishimoyama, I. et al., "The Finger-Tapping Test, A Quantitative Analysis," Arch Neurol. 1990;47(6):681-684.
International Search report for PCT/EP2018/073843 dated Sep. 5, 2018.

* cited by examiner

METHOD AND APPARATUS FOR IMPROVING THE MEASUREMENT OF THE TIMING OF TOUCHES OF A TOUCH SCREEN

CROSS-REFERENCE TO PRIOR APPLICATIONS

This application is the U.S. National Phase application under 35 U.S.C. § 371 of International Application No. PCT/EP2018/073843, filed on Sep. 5, 2018, which claims the benefit of European Patent Application No. 17189896.8, filed on Sep. 7, 2017. These applications are hereby incorporated by reference herein.

TECHNICAL FIELD OF THE INVENTION

The invention relates to a method and apparatus for improving the measurement of the timing of touches of a touch screen.

BACKGROUND TO THE INVENTION

Psychological tests may be employed to assess cognitive/mental performance of a user. Examples of such tests included the Psychomotor Vigilance Test (PVT) and the Finger Tapping Task (FTT).

The PVT is a reaction time test used to assess sleepiness or alertness, where a user presses a button as quickly as possible in response to a visual or auditory stimulus. This visual or auditory stimulus is typically presented every few seconds for a period of 5 to 10 minutes. There are a number of parameters that are relevant for the PVT that can indicate the level of sleepiness or alertness of the user. For example, the reaction time to the stimulus can be assessed (e.g. the mean, median and standard deviation of the reaction times, the slowest response time, the fastest response time, etc.). The trend of the reaction time as a function of time can provide an indication of the deterioration of alertness. The number of missed stimuli (i.e. no response from the user) can be assessed, and also or alternatively the number of "false starts" (i.e. the user responds before the stimulus is generated).

The FTT is a test of psychomotor performance. In the "time tap" form a user is asked to repeatedly press a button as quickly as possible for a fixed amount of time, for example 10 seconds. Usually repeated trials are administered. In the "rhythm tap" form a user is asked to tap a button each time they hear a tone or see a light flash, which is presented with a consistent rhythm. Then, the user must continue tapping in this rhythm after the stimulus has ceased. Relevant parameters for assessing the performance of the Finger Tapping Task include the tap speed (the number of taps per trial), the rhythm (the percentage of time that the rhythm is maintained) and the reaction time (to first response).

The PVT or FTT are often administered using dedicated hardware, e.g. for the PVT a computer controlled stimulus, e.g. a red LED, and a physical button can be provided, with the computer accurately determining the reaction time.

It is desirable for tests such as the PVT and FTT to be performed easily and/or frequently by a user in their home environment, or otherwise during their normal daily living activities. As such, the need for dedicated hardware and/or software should be minimised or avoided. In particular, it is desirable to implement tests such as the PVT and FTT in consumer electronic devices, e.g. in smartphones or tablets, since in principle these tasks lend themselves to being implemented using these devices. Instructions and visual and/or auditory stimuli can easily be provided using an electronic device. Furthermore, the touch screen typically found on such an electronic device can be used to register the response of the subject, thereby avoiding the need for a dedicated button.

However, there is a practical issue associated with the use of a touch screen for such tasks, and that is the accuracy of the timing of the detected touches. The touch screens of electronic devices often employ a scanning strategy to assess whether the user is touching the screen. This results in multiple sources of error, which makes the touch screen less suitable for this type of task. For example the sampling frequency of touch screens is often very low, e.g. around 10 Hz, reducing the resolution possible for any detected touch. In addition, due to the scanning of the touch screen matrix, the response time will be affected by the actual position where the touch screen is touched (this is known as position dependency). Another source of error is jitter since the timing of touch screen events is jittery. This jitter can originate from both poor performance of the touch screen as well as the priority given to processing touch screen events by the operating system of the electronic device.

SUMMARY OF THE INVENTION

Thus, it is desirable to be able to implement a reaction time-based task using an electronic device having a touch screen for receiving the reaction inputs from the user. Such tests require touch timings at a level of accuracy that are not provided by conventional touch screens. To address or mitigate the issues with the inaccuracy of the touch timings provided by the touch screen, it is proposed instead to derive timings for touches of a touch screen using a signal from a sensor that can measure the touch action by the user. These timings can be used as part of a finger tapping task to more accurately determine the time between taps, and/or they can be used to determine the reaction time of the user to a stimulus.

According to a first aspect, there is provided a method of determining a time at which a user touched a touch screen of an electronic device, the method comprising obtaining a touch signal generated by the touch screen for a first time period, the touch signal indicating when the user touched the touch screen during the first time period; obtaining a sensor signal generated by a first sensor for at least the first time period, the sensor signal comprising a first signal component corresponding to a measurement by the first sensor of the user making contact with the touch screen; using the touch signal to identify a time window in the sensor signal containing the first signal component; and processing the windowed sensor signal to determine the timing of the first signal component in the sensor signal. It is an advantage of the present invention to provide for a more accurate timing of the touch of the touch screen.

In some embodiments, the step of using the touch signal to identify the time window comprises generating a pulse signal from the touch signal, each pulse in the pulse signal corresponding to a detected touch in the touch signal; generating a characteristic signal for the sensor signal; correlating the pulse signal and the characteristic signal to generate a delayed pulse signal; and using the delayed pulse signal to identify the time window in the sensor signal.

In some embodiments, the step of processing the windowed sensor signal comprises using a thresholding, pattern matching or correlation algorithm to identify the first signal component in the sensor signal.

In some embodiments, the method further comprises using the determined timing of the first signal component as the time at which the user touched the touch screen. This determined timing can be used in reaction tasks, finger tapping tasks, other tasks, tests, programs or activities where more precise touch timing is useful.

In some embodiments, the method further comprises determining a signal processing delay relating to the first sensor; and determining the time at which the user touched the touch screen based on the determined timing of the first signal component and the determined signal processing delay. This embodiment has an advantage that a signal processing delay associated with, for example, the amplification and conversion of an analogue sensor signal to a digital signal suitable for processing is recognised and compensated for when determining the timing of the touch.

In some embodiments, the method further comprises obtaining an excitation signal used as an input to a first transducer to generate a first stimulus; with the sensor signal further comprising a second signal component corresponding to a measurement by the first sensor of the first stimulus or corresponding to a measurement by the first sensor of a second stimulus generated at the same time as the first stimulus. In this case the step of using comprises using the excitation signal and the touch signal to identify the time window in the sensor signal that contains the first signal component and the second signal component; and the step of processing further comprises processing the windowed sensor signal to determine the timing of the second signal component. Thus, these embodiments provide the advantage that the improved timing accuracy of the detected touches can be used to improve the measurement of a user's reaction time to a stimulus.

In some embodiments, the method further comprises the step of generating the first stimulus using the first transducer.

In some embodiments, the step of using sing the touch signal to identify the time window comprises correlating the excitation signal and the sensor signal to determine a delay between the first stimulus or the second stimulus and the second signal component; removing the second signal component from the sensor signal to generate a filtered sensor signal; generating a characteristic signal for the filtered sensor signal; generating a pulse signal from the touch signal, each pulse in the pulse signal corresponding to a detected touch in the touch signal; correlating the pulse signal and the characteristic signal to generate a delayed pulse signal; and using the delayed pulse signal to identify the time window in the sensor signal.

In some embodiments, the method further comprises generating the second stimulus using a second transducer at the same time that the first transducer generates the first stimulus, wherein the second stimulus is a different type of stimulus to the first stimulus. This embodiment is useful where, for example, the first stimulus is not perceptible to the sensor, and a different type of stimulus is required in order to be measured by the sensor.

In some embodiments, the method further comprises determining the reaction time of the user to the first stimulus from the timing of the first signal component and the timing of the second signal component. It is an advantage of the present invention to provide for the reaction time determinable just from the sensor signal.

In some embodiments, the method further comprises estimating the time taken for the first stimulus to travel from the first transducer to the user; and the reaction time of the user to the first stimulus is determined from the timing of the first signal component, the timing of the second signal component and the estimate of the time taken. These embodiments further improve the accuracy of the reaction time by taking into account the time taken for the first stimulus to propagate from the first transducer to the user.

In various embodiments, the first transducer and/or second transducer can be a loudspeaker, headphones, a light source or a vibrating component. In various embodiments, the first stimulus and/or second stimulus can be an audible stimulus, a visual stimulus or a tactile stimulus. In various embodiments, the first sensor can be a microphone or a movement sensor in the electronic device.

According to a second aspect, there is provided a computer program product comprising a computer readable medium having computer readable code embodied therein, the computer readable code being configured such that, on execution by a suitable computer or processor, the computer or processor is caused to perform any of the methods described above.

According to a third aspect, there is provided an apparatus for determining a time at which a user touched a touch screen of an electronic device, the apparatus comprising a processing unit configured to obtain a touch signal generated by the touch screen for a first time period, the touch signal indicating when the user touched the touch screen during the first time period; obtain a sensor signal generated by a first sensor for at least the first time period, the sensor signal comprising a first signal component corresponding to a measurement by the first sensor of the user making contact with the touch screen; use the touch signal to identify a time window in the sensor signal containing the first signal component; and process the windowed sensor signal to determine the timing of the first signal component in the sensor signal. Thus, a more accurate timing of the touch of the touch screen is obtained.

In some embodiments, the processing unit is configured to use the touch signal to identify a time window by generating a pulse signal from the touch signal, each pulse in the pulse signal corresponding to a detected touch in the touch signal; generating a characteristic signal for the sensor signal; correlating the pulse signal and the characteristic signal to generate a delayed pulse signal; and using the delayed pulse signal to identify the time window in the sensor signal.

In some embodiments, the processing unit is configured to process the windowed sensor signal using a thresholding, pattern matching or correlation algorithm to identify the first signal component in the sensor signal.

In some embodiments, the processing unit is further configured to use the determined timing of the first signal component as the time at which the user touched the touch screen. This determined timing can be used in reaction tasks, finger tapping tasks, other tasks, tests, programs or activities where more precise touch timing is useful.

In some embodiments, the processing unit is further configured to determine a signal processing delay relating to the first sensor; and determine the time at which the user touched the touch screen based on the determined timing of the first signal component and the determined signal processing delay. This embodiment has an advantage that a signal processing delay associated with, for example, the amplification and conversion of an analog sensor signal to a digital signal suitable for processing is recognised and compensated for when determining the timing of the touch.

In some embodiments, the processing unit is further configured to obtain an excitation signal used as an input to a first transducer to generate a first stimulus; with the sensor signal further comprising a second signal component corresponding to a measurement by the first sensor of the first stimulus or corresponding to a measurement by the first sensor of a second stimulus generated at the same time as the first stimulus. In this case the processing unit is configured to use the excitation signal and the touch signal to identify the time window in the sensor signal that contains the first signal component and the second signal component; and the processing unit is configured to process the windowed sensor signal by processing the windowed sensor signal to determine the timing of the second signal component. Thus, these embodiments provide the advantage that the improved timing accuracy of the detected touches is used to improve the measurement of a user's reaction time to a stimulus.

In some embodiments, the apparatus further comprises a first transducer that is responsive to the excitation signal to generate the first stimulus.

In some embodiments, the processing unit is configured to use the touch signal to identify a time window in the sensor signal by correlating the excitation signal and the sensor signal to determine a delay between the first stimulus or the second stimulus and the second signal component; removing the second signal component from the sensor signal to generate a filtered sensor signal; generating a characteristic signal for the filtered sensor signal; generating a pulse signal from the touch signal, each pulse in the pulse signal corresponding to a detected touch in the touch signal; correlating the pulse signal and the characteristic signal to generate a delayed pulse signal; and using the delayed pulse signal to identify the time window in the sensor signal.

In some embodiments, the apparatus further comprises a second transducer for generating a second stimulus at the same time that the first transducer generates the first stimulus, wherein the second stimulus is a different type of stimulus to the first stimulus. This embodiment is useful where, for example, the first stimulus is not perceptible to the sensor, and a different type of stimulus is required in order to be measured by the sensor.

In some embodiments, the processing unit is further configured to determine the reaction time of the user to the first stimulus from the timing of the first signal component and the timing of the second signal component. Thus, these embodiments provide that the reaction time can be determined just from the sensor signal.

In some embodiments, the processing unit is further configured to estimate the time taken for the first stimulus to travel from the transducer to the user; and determine the reaction time of the user to the first stimulus from the timing of the first signal component, the timing of the second signal component and the estimate of the time taken. These embodiments further improve the accuracy of the reaction time by taking into account the time taken for the stimulus to propagate from the transducer to the user.

In various embodiments, the first transducer and/or the second transducer can be a loudspeaker, headphones, a light source or a vibrating component. In various embodiments, the first stimulus and/or second stimulus can be an audible stimulus, a visual stimulus or a tactile stimulus. In various embodiments, the first sensor can be a microphone or a movement sensor in the electronic device.

These and other aspects of the invention will be apparent from and elucidated with reference to the embodiment(s) described hereinafter.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

As noted above, it is desirable to be able to implement a reaction time-based task or repetitive motion-based task on an electronic device (or indeed any type of device) having a touch screen for receiving inputs from the user. To address or mitigate the issues with the inaccuracy of the touch timings provided by the touch screen, it is proposed to derive timings for touches of a touch screen using a signal from a sensor that can measure the touch action by the user. These timings can be used as part of a finger tapping task to more accurately determine the time between taps, and/or they can be used to determine the reaction time of the user to a stimulus.

In some embodiments, the sensor is a microphone that can measure the sound of the user touching the touch screen (and also the sound of the stimulus if an audible stimulus is used). In some embodiments, the sensor is an accelerometer and/or gyroscope that can measure the movement or vibration caused by the user touching the touch screen (and also a vibration stimulus if a vibration stimulus is used). The accelerometer and/or gyroscope can be part of the electronic device or the accelerometer and/or gyroscope can be part of a user-worn device (e.g. a smart watch).

Motion sensors, such as accelerometers and gyroscopes typically sample at frequencies of 100 Hz or higher. For microphones, recording sample rates are even higher (e.g. 8 kHz for narrowband speech, or 16 kHz for wideband speech). Furthermore, compared to a touch screen that often samples at the display refresh rate, sample rate jitter for motion sensors and microphones is relatively low. Therefore, data captured by such sensors allows for a much more accurate representation of the actual timing of an interaction with the touch screen by a user, enabling implementation of psychological tasks on electronic devices.

Figure 1:
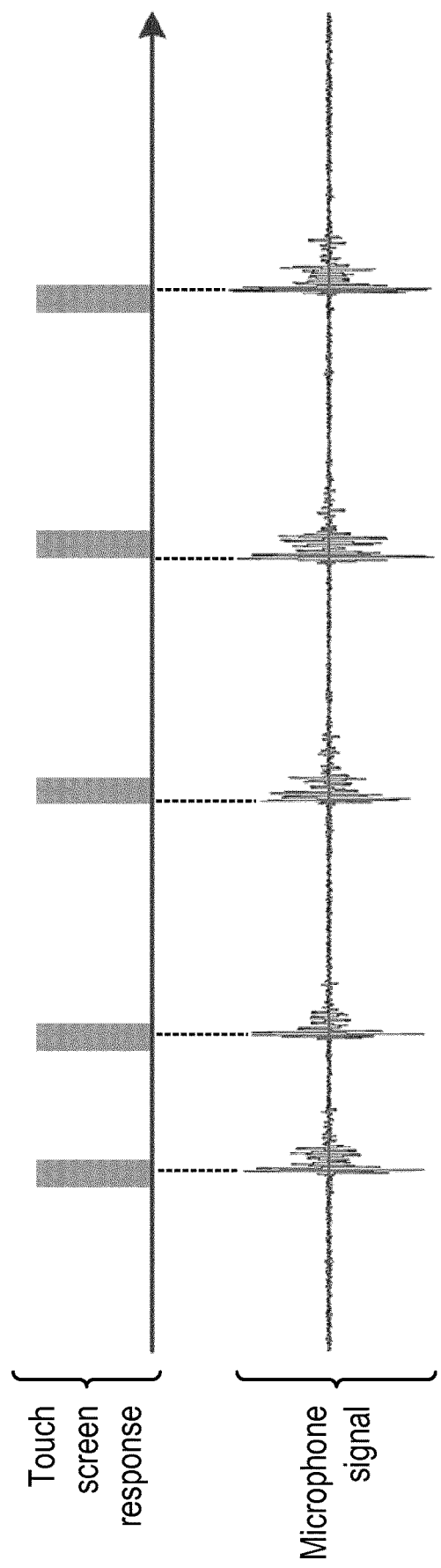
FIG. 1 is a graph illustrating a signal from a touch screen and a signal from a microphone.

FIG. 1 is a graph illustrating a signal received from a touch screen of an electronic device (the upper line) and a signal covering the same time period received from a microphone in the same device (the bottom line). The graph covers a time period in which the user touches the touch screen five times. The detected touch events are clearly visible in the touch screen signal (which is also referred to herein as a 'touch signal'), and the sounds of the user touching or tapping the touch screen are also visible in the microphone signal. The detected touch events and detected touch sounds are aligned (on average). Ideally the timing of the touch screen presses should be fully in sync (or with a fixed delay) with the touch sounds measured in the microphone signal. However, as can be seen, the touch screen timings, each denoted by a rectangle (with the left side of the rectangle indicating the start time of the touch, and the right side of the rectangle indicating the end time of the touch) do not correspond very well to the data captured by the microphone due to issues with jitter and scanning as explained above.

Figure 2:
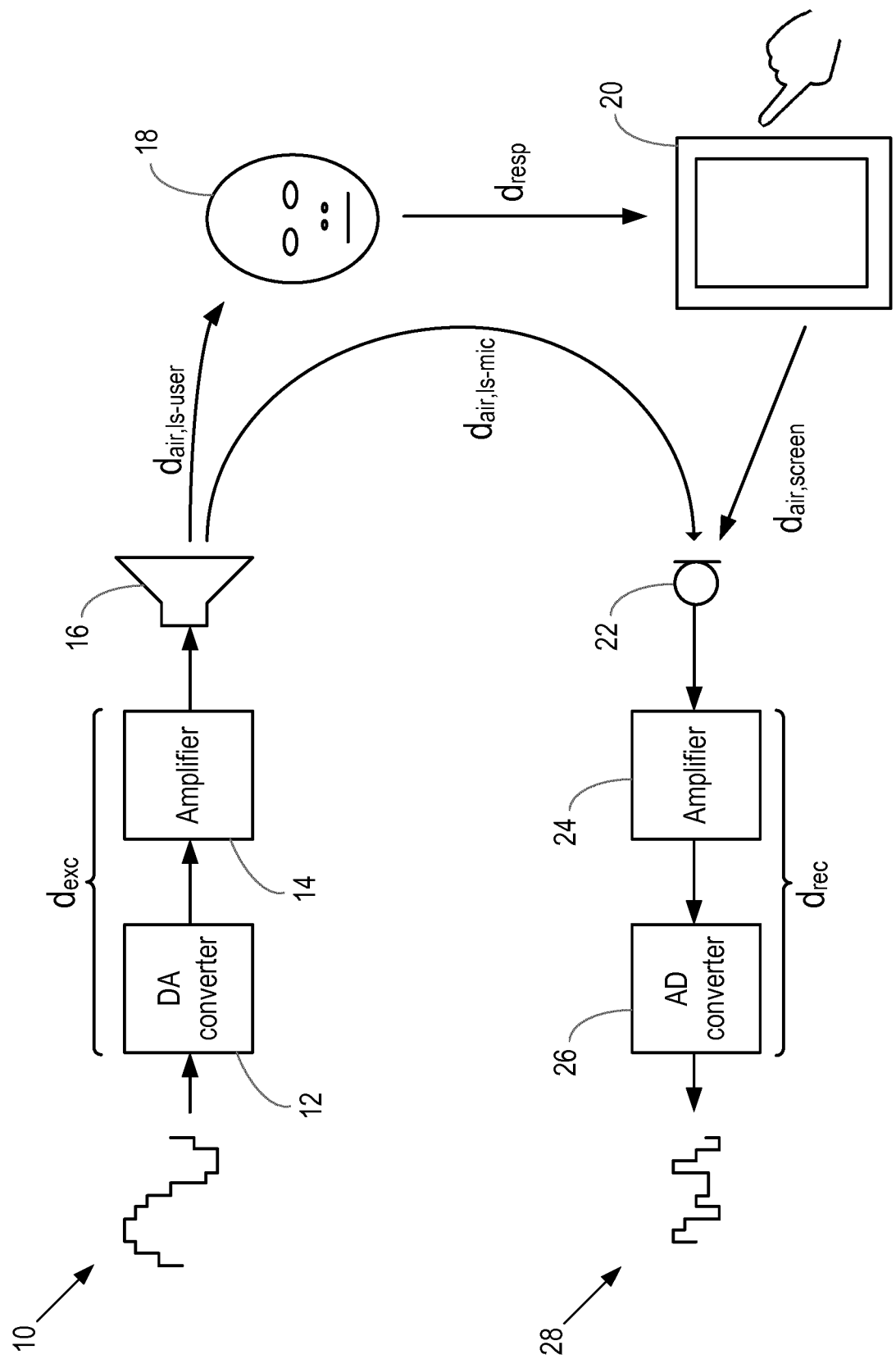
FIG. 2 is a block diagram illustrating the signal path in a test with an audible stimulus.

In a specific implementation of the invention, an auditory PVT task is performed using both the timing provided by a touch screen and a microphone signal. As described above, the auditory PVT task is a reaction time task based on auditory stimuli, typically consisting of a beep. This beep is either played to the user through a loudspeaker or through headphones. The task of the user is to respond as quickly as possible to these stimuli by pressing a button, which, in the case of a device with a touch screen, is the touch screen. The device can also include a microphone that can record (i.e. measure) the sound of the audible stimulus and also the sound of the user touching the touch screen. Various aspects of the signal path between the loudspeaker, user and microphone are explained below with reference to FIG. 2. In FIG. 2, it is assumed that the loudspeaker, touch screen and microphone are all part of the same device, but in practice this is not required.

A digital auditory stimulus (i.e. a beep) in the form of a sample train 10 is generated. This signal is converted to the analog domain via a digital to analog (DA) converter 12. The analog signal is subsequently amplified by amplifier 14 and output by the loudspeaker 16. The loudspeaker 16 creates air pressure waves (i.e. sound) that are received by the human auditory system (indicated by user 18). Upon interpretation of the sound, the user 18 presses the touch screen 20 as quickly as possible. The timing of the touch screen press is registered in the device.

A microphone 22 of the device captures all audio starting from the production of the beep up until at least the time of the detected touch screen press. The analog microphone signal is amplified by amplifier 24 and converted to the digital domain by analog to digital (AD) convertor 26 for further processing. The digital signal representing the output of the microphone is shown as signal 28.

The volume of the stimuli may vary over time, to test for alertness, but may also have a constant volume.

Figure 3:
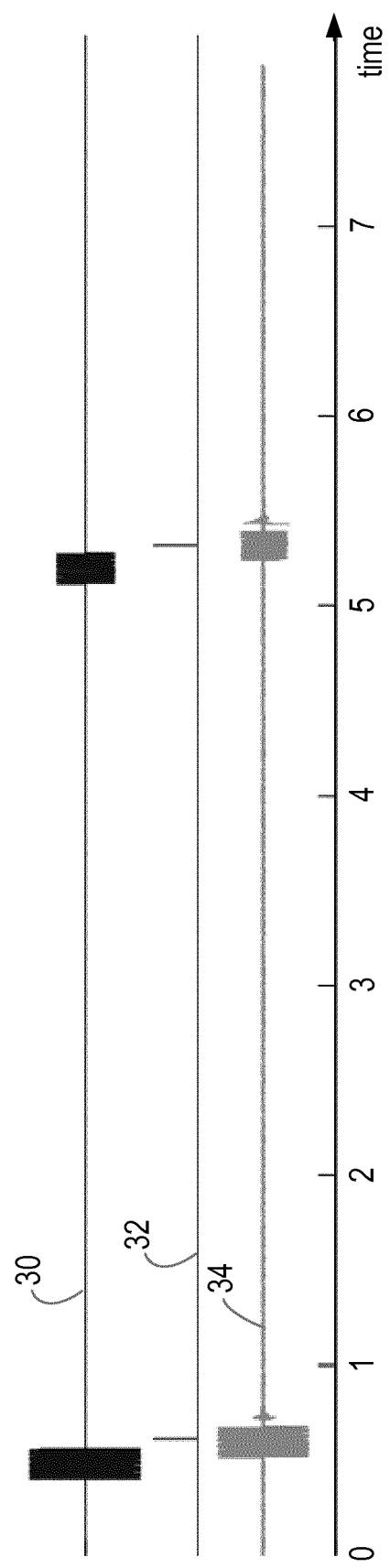
FIG. 3 is a graph showing a stimulus excitation signal, a signal from a touch screen and a signal from a microphone.

The graph in FIG. 3 shows an exemplary stimulus excitation signal, a signal from a touch screen 20 and a signal from a microphone that can be obtained using the arrangement shown in FIG. 2. Signal 30 is an excitation signal (corresponding to sample train 10 in FIG. 2) in which the volume of the stimulus changes over time. Signal 30 represents the excitation stimulus as it is sent to the loudspeaker 16 via the DA converter 12 and amplifier 14. The excitation signal 30 consists of two fixed frequency beeps at two different amplitudes (e.g. to test for alertness). Signal 32 is the output of the touch screen 20 showing two detected touch screen presses by the user 18. Signal 34 is the microphone signal (corresponding to signal 28 in FIG. 2). As can be seen, in the microphone signal 34 both the two audible stimuli and the two presses of the touch screen 20 are present. In addition to the audible stimuli and presses of the touch screen 20, some other noise is present.

It can be seen from FIG. 3 that the presses of the touch screen 20 recorded in the microphone signal 34 are not aligned in time with the detected touch screen presses in the touch screen signal 32. This is due in part to the timing inaccuracy of the touch screen 20, but also several delays in the signal path, as explained below.

In the explanation below, the following notations for time are used:

$t_0$—the absolute time of the start of the stimulus 10/30 when the digital train of audio samples 10 is being generated;

$t_1$—the absolute time at which the loudspeaker 16 starts to produce the audible stimulus;

$t_2$—the absolute time at which the user 18 presses the touch screen 20; and $t'_2$—the time at which the user 18 presses the touch screen according to the touch screen signal (due to the timing inaccuracy of the touch screen, it will be appreciated that $t'_2$ only approximates the absolute time at which the user 18 touched the touch screen 20).

The actual response or reaction time of the user 18 is the time it takes from the user 18 to receive the sound (so the stimulus signal is present at the human auditory system) up until the time the user 18 has pressed the touch screen 20. Of course, sound travelling through the air also takes a certain amount of time. The time difference between the sound leaving the loudspeaker 16 and hitting the eardrums of the user 18 is denoted $d_{air,ls\text{-}user}$. This time difference or delay is shown in FIG. 2.

Using the assumption that the stimulus is provided to the user 18 using headphones, which is typical for the PVT, the time taken for the sound to travel from the loudspeaker to the human auditory system is negligible (since the loudspeakers in the headphones are very close to the ears). It will be appreciated that in headphone embodiments, the digitised and amplified excitation signal 10 can be used to drive a loudspeaker (separate from the headphones) so that the audible stimulus can be recorded by the microphone 22, although it will also be appreciated that it could be possible for the microphone 22 to record the audible stimulus directly from the headphones if there is some leakage of sound from the headphones (which is quite typical).

When headphones are not used, in some embodiments it can be assumed that the time that the sound travels through the air to the user is constant (i.e. the distance between the loudspeaker 16 and the user 18 is fixed). In other embodiments, an estimate of the propagation time $d_{air,ls\text{-}user}$ can be made. In one embodiment it would be possible to employ a camera (e.g. that is part of the same device as the touch screen 20 to estimate the distance of the user from the touch screen 20 by making use of face detection technology. Through knowledge of the distance of certain features (e.g. the distance between both eyes), expressed in screen pixels, an estimate of the distance can be made.

Since the user 18 cannot respond/react before the sound reaches the ear drum, a good definition of the response (reaction) time is:

$$d_{resp} = t_2 - t_1 - d_{air,ls\text{-}user} \qquad (1)$$

The following timings are also defined:

$t^m_1$—the absolute time at which the digital train of audio samples 28/34 derived from the analog microphone signal starts representing the audio stimulus (beep);

$t^m_2$—the absolute time at which the digital train of audio samples 28/34 derived from the analog microphone signal starts representing the pressing of the touch screen 20;

$d_{exc}$—the excitation delay; the time delay caused by DA converting and amplifying the digital train of audio samples 10/30 on the loudspeaker side ($d_{exc}$ is shown in FIG. 2);

$d_{air,ls\text{-}mic}$—the delay due to the transmission over the air from the loudspeaker 16 to the microphone 22 ($d_{air,ls\text{-}mic}$ is shown in FIG. 2);

$d_{rec}$—the recording delay; the time delay caused by amplifying and AD converting the analog signal from the microphone 22 to the digital train of samples 28/34 ($d_{rec}$ is shown in FIG. 2); and $d_{round}$—the round trip delay from the generation of the digital stimulus signal 10/30 to generating the digital microphone signal 28/34. It will be appreciated that $d_{round} = d_{exc} + d_{air,ls-mic} + d_{rec}$.

The touch screen signal will only be able to provide a rough estimate of $t_2$, namely $t'_2$. A typical approximation of the reaction/response time of the user 18 to the stimulus (denoted $d_{resp}$) would be:

$$d_{resp} = t'_2 - t_0 \quad (2)$$

where, as defined above, $t'_2$ is the detected touch timing derived from the touch screen 20, and to is derived from the start of the generation of the audio stimulus signal.

Alternatively, if an approximation of the delay in the excitation path, $d_{exc}$, is known, then the response/reaction time can be determined using:

$$d'_{resp} = t'_2 - t_0 - d_{exc} \quad (3)$$

It should be noted that with some effort an estimate of $d_{exc}$ can be made, either from the specification of the components used in the excitation path (i.e. the DA converter 12, the amplifier 14, and/or the loudspeaker(s) 16), or by simultaneously capturing the input to the DA convertor 12 and the signal at the loudspeaker(s) 16, e.g. during manufacture or during calibration of the device. It should be noted that $d_{exc}$ is device (e.g. model/brand) specific. In addition it should be noted that $d'_{resp}$ is still an erroneous estimate of the actual response time of the user 18 due to jitter, dependence on the touch screen scanning strategy and the low sampling frequency of the touch screen 20.

Using the microphone signal 28/34, it is possible to derive a more accurate estimate of the reaction time. By definition, the time at which the digital microphone signal 28/34 starts representing the press of the touch screen 20 is:

$$t''_2 = t_2 + d_{air,screen} + d_{rec} \quad (4)$$

where $d_{air,screen}$ is the time the sound takes to travel from the touch screen 20 to the microphone 22 (as shown in FIG. 2). It will be appreciated that this transmission does not necessarily need to take place via the air, but may also be due to vibrations of the electronic device itself.

The time $t'''_1$ is given by:

$$t'''_1 = t_1 + d_{air,ls-mic} + d_{rec} \quad (5)$$

Looking at the time difference between $t'''_2$ and $t'''_1$, we have:

$$t'''_2 - t'''_1 = t_2 + d_{air,screen} - t_1 - d_{air,ls-mic} \quad (6)$$

and using:

$$d_{resp} = t_2 - t_1 - d_{air,ls-user} \quad (7)$$

we get:

$$t'''_2 - t'''_1 = d_{resp} + d_{air,ls-user} + d_{air,screen} - d_{air,ls-mic} \quad (8)$$

and so the accuracy of the estimate of the response time ($d_{resp}$) only depends on the time that the sound travels through the air.

In a first specific case, audio can be output via loudspeaker, for example a loudspeaker of the electronic device that has the touch screen. In this case, $d_{air,screen}$ and $d_{air,ls-mic}$ are negligible, and will effectively cancel each other if the path lengths are more or less equal. If the arrangement of the user 18 and loudspeaker 16 is such that there is an approximately fixed distance from the head of the user 18 to the electronic device, as is typically the case, the time the sound takes to travel from the loudspeaker 16 to the user, may actually be included in the definition of the response time.

In a second specific case, audio is output via headphones (which can be connected to the electronic device having the touch screen 20). In this case, $d_{air,ls-user}$ is negligible (since it is effectively only the distance along the ear canal) as well as $d_{air,screen}$. The dominant disturbing factor is the delay in the headphones audio signal to the microphone 22. It can be assumed that there is a constant distance between the headphones and microphone. However, since it will be technically more challenging to detect the audible stimulus generated by the headphones at the microphone 22, especially when closed headphones are used, it may be preferable to estimate $t_1$ from $t_0 + d_{exc}$. It should be noted that the above case relates to wired headphones. If wireless headphones are used, then there will be an additional delay caused by the transmission of the audio through the wireless connection.

The above description assumes that the individual touches in the microphone signal are known. However, the microphone signal will also pick up noise from the environment (e.g. caused by the user 18) and so the touches in the microphone signal need to be detected. Thus, according to embodiments of the invention, the information in the touch screen signal can be used to identify the touches in the microphone signal. Since the microphone 22 has a much higher sampling resolution than the touch screen 20, the accuracy of the timing of the touches identified in the microphone signal will be better than that provided by the touch screen signal. Further details of these embodiments are provided below. More generally, information in a touch screen signal can be used to identify the touches in the signal from another sensor that can detect the user touching the touch screen (e.g. a microphone, an accelerometer, a gyroscope, etc.).

First, an apparatus 40 in which the invention can be implemented is described with reference to FIG. 4. The apparatus 40 comprises a processing unit 42 and a memory unit 44. The processing unit 42 is configured or adapted to control the operation of the apparatus 40 and to implement the techniques according to the invention for determining the timing of a touch of a touch screen.

The processing unit 42 can be implemented in numerous ways, with software and/or hardware, to perform the required function(s). The processing unit 42 may comprise one or more microprocessors that may be programmed using software to perform the required functions. The processing unit 42 may be implemented as a combination of dedicated hardware to perform some functions and a processor (e.g., one or more programmed microprocessors and associated circuitry) to perform other functions. Examples of components that may be employed in various embodiments of the present disclosure include, but are not limited to, conventional microprocessors, application specific integrated circuits (ASICs), and field-programmable gate arrays (FPGAs).

The memory unit 44 can store program code that can be executed by the processing unit 42, and for example computer code that can cause or allow the processing unit 42 to implement the techniques according to the invention. The memory unit 44 can also or alternatively store information or signals required during the implementation of the techniques according to the invention, for example the signals from a touch screen and/or sensor (such as a microphone or accelerometer). The memory unit 44 can also or alternatively store information on the results of the invention, such as the timing of detected touches, the timing between consecutive touches, the reaction times to a stimulus, etc. The memory unit 44 can comprise any suitable type of non-volatile or volatile memory, including, but not limited to, magnetic-based storage, such as a hard disk, solid-state memory, or optical-based storage, such as an optical disk.

The apparatus 40 may be in the form of a smart phone, tablet, laptop, computer, server, or any other type of electronic device that can process a signal from a touch screen and a signal from another sensor to determine the timing of a touch of the touch screen by a user. It will be appreciated that the apparatus 40 does not have to be the same device as that comprising the touch screen and sensor, but in some embodiments the apparatus 40 is part of the device that does include the touch screen and sensor.

Figure 4:
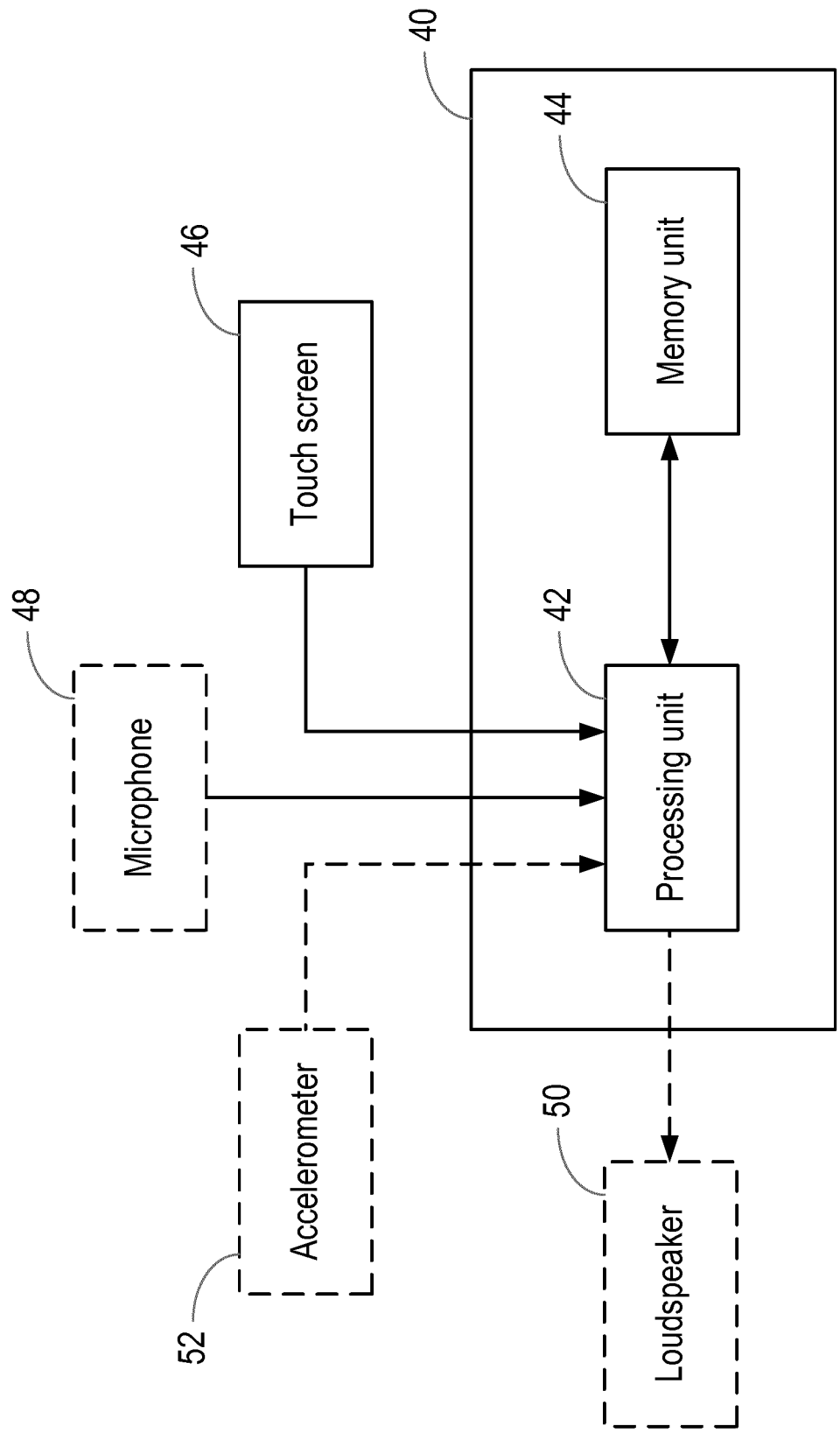
FIG. 4 is a block diagram of an apparatus according to an embodiment of the invention.

In addition to the apparatus 40, FIG. 4 shows a touch screen 46 (which as noted above may or may not be part of the apparatus 40), which can receive and measure touches or touch inputs by a user. The touch screen 46 outputs a signal representing the touches by the user that is used by the processing unit 42. This signal is referred to as a 'touch screen signal' herein. It will be appreciated that the touch screen signal does not have to be provided to the processing unit 42 in real time (although this is possible), instead the touch screen signal can be provided at the end of a test (e.g. at the end of the PVT or FTT), or some time after the test is completed.

FIG. 4 also shows a microphone 48 that is used to measure or record the sound of the user pressing or touching the touch screen 46 and that provides the signal to the processing unit 42. Although not shown in FIG. 4, the processing unit 42 processes a digital representation of the audio signal recorded by the microphone 48, and so either the microphone 48 or the apparatus (e.g. the processing unit 42) comprises an amplifier and an AD convertor. The digital signal from the microphone 48 is referred to as the 'microphone signal' hereinafter. It will be appreciated that in some embodiments the microphone 48 is not required, as the touches of the touch screen 46 can instead by detected by a movement sensor, such as an accelerometer or gyroscope. Therefore FIG. 4 shows an optional accelerometer 52 that is connected to the processing unit 42. The signal from the accelerometer 52 (or movement sensor) is referred to as the 'accelerometer signal' (or 'movement signal') herein. In some embodiments, both the microphone 48 and accelerometer 52 are used.

The microphone 48, accelerometer 52 and/or gyroscope can more generally be referred to as a sensor that generates a sensor signal that comprises a signal component corresponding to a measurement by the sensor of the user making contact with the touch screen 46.

It will be appreciated that any of the microphone 48, accelerometer 52 and/or gyroscope (whichever is present) may be in the same device as the touch screen 46, or a different device. As described in more detail below, in some embodiments the processing unit 42 can receive an accelerometer signal from an accelerometer in a device that is being worn by the user (e.g. a smart watch).

Finally, FIG. 4 also shows a transducer 50 in the form of a loudspeaker that can be used in some embodiments to provide an audible stimulus that the user is to react to. The loudspeaker 50 is shown as being connected to the processing unit 42, although in some embodiments the processing unit 42 may simply receive the excitation signal used to drive the loudspeaker 50 to produce the audible stimulus without being connected to the loudspeaker 50 itself. As with the sensor(s) 48, 52 above, the loudspeaker 50 may be part of the apparatus 40, or part of another device.

In alternative embodiments where a stimulus other than an audible stimulus is used, e.g. a light-based stimulus, or a vibration-based stimulus, a loudspeaker 50 may optionally not be present, and instead a light or vibrating transducer 50 can be provided. In either case the apparatus 40 can receive an excitation signal for the component that generates the stimulus for the user.

It will be appreciated that the apparatus 40 may comprise other components to those shown in FIG. 4. For example the apparatus 40 may comprise a power supply (such as a battery) or an interface for connection to a mains power supply. In another example, the apparatus 40 may comprise a user interface component for presenting the results of the processing according to the invention to the user or another interested party, such as a healthcare provider. In some embodiments, the user interface component can be the touch screen 46.

As noted above, the invention provides that information in a touch screen signal is used to identify the touches in a signal from a sensor that can measure the effect of the user touching the touch screen 46 (e.g. the sound of the user touching the touch screen 46, or the vibration or movement of the touch screen 46 as the user touches it).

Figure 5:
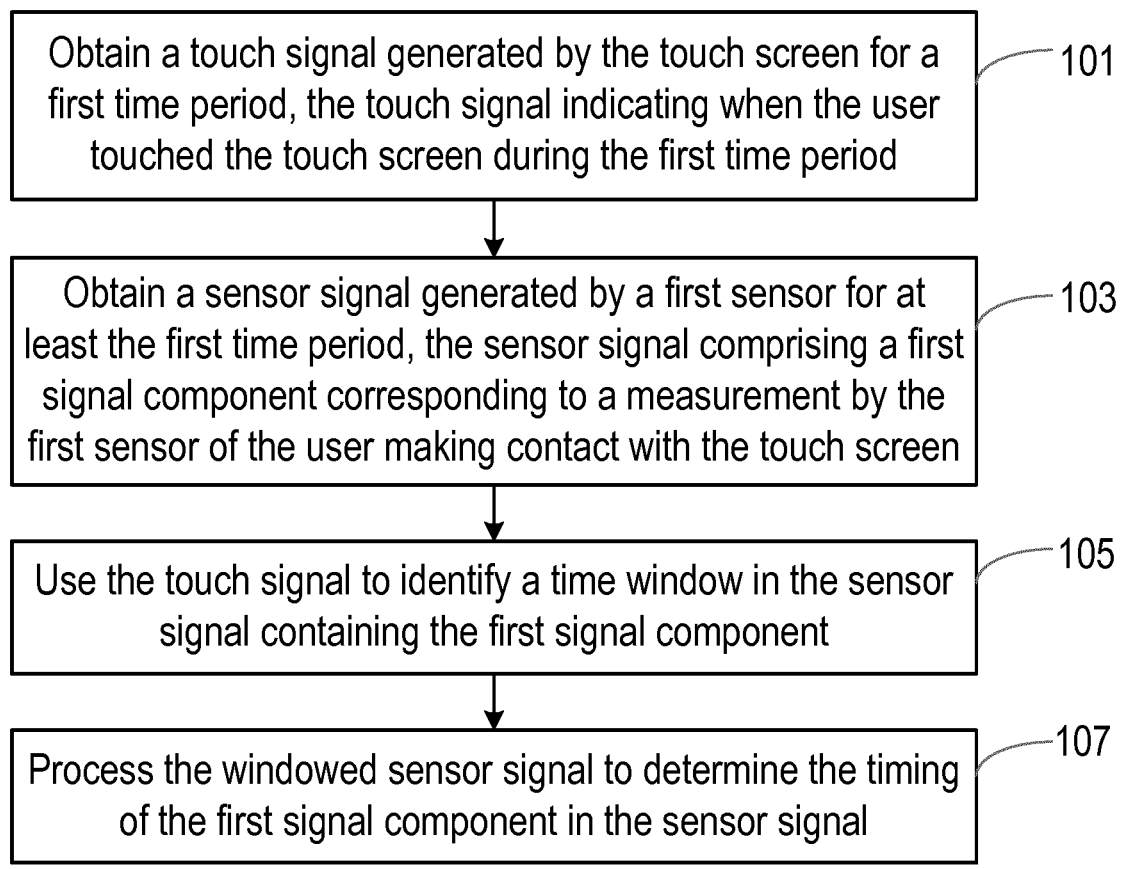
FIG. 5 is a flow chart illustrating a method of determining the timing of a touch of a touch screen according to an embodiment of the invention.

The flow chart in FIG. 5 illustrates an exemplary method of determining a time at which a user touched a touch screen 46 according to the invention. The method in FIG. 5 can be performed by the apparatus 40, in particular the processing unit 42.

In a first step, step 101, a touch signal generated by the touch screen 46 is obtained. The touch signal covers a first time period which includes one or more touches of the touch screen 46 by the user. The touch signal indicates when the user touched the touch screen 46 during the first time period.

In a second step, step 103 (which can be performed before, after or at the same time as step 101), a sensor signal generated by a sensor 48, 52 is obtained. As noted above, the sensor signal can be a microphone signal and/or an accelerometer signal and/or a gyroscope signal. The sensor signal covers at least part of the first time period in which the user touched the touch screen, and so the sensor signal includes a first signal component corresponding to a measurement by the sensor 48, 52 of the user making contact with the touch screen 46.

It will be appreciated that the signals in steps 101 and 103 can be obtained by the processing unit 42 receiving the signals directly from the touch screen 46 and sensor 48, 52 respectively, or by retrieving the signals from the memory unit 44 or from another device.

Next, in step 105, since the sensor signal will not only comprise the signal component corresponding to the touch of the touch screen 46 by the user (e.g. it will contain noise and/or signal components corresponding to other sounds or movements of the touch screen 46 or movements of the device in which the touch screen 46 is comprised), the processing unit 42 uses the touch signal to identify a time window in the sensor signal that contains the first signal component.

In particular, the processing unit 42 can identify the approximate timing of a touch of the touch screen 46 ($t'_2$) as indicated by the touch screen signal, and use that timing to select (i.e. window) a part of the sensor signal that includes that time.

The width of the window around a detected touch can be set to any desired value, for example the width of the window can be set to a value that corresponds to a timing uncertainty for touches in the touch signal. E.g. if it is known that a touch in the touch screen signal is only accurate to 0.2 seconds, then the window can have a width of 0.2 seconds centred on the detected touch. In some embodiments, the width of the window is the sum of the typical length of a detected touch in the sensor signal and the width of the maximum expected timing uncertainty. This can provide a window that has a length of the order of 10 ms-100 ms. In some embodiments, since there may be a processing delay caused by pre-processing of the sensor signal (e.g. amplification and AD conversion in the case of a microphone 48) compared to the touch screen signal, this delay can be taken into account when applying the window generated from the touch screen signal to the sensor signal. The delay in the processing may be known (e.g. determined during manufacture or calibration of the electronic device or other device comprising the first sensor 48, 52) or can be estimated in embodiments where a stimulus is provided to the user and the stimulus can also be measured by the first sensor 48, 52).

Once the time window has been identified, in step 107, the processing unit 42 then processes the windowed sensor signal (i.e. the part of the sensor signal in the window) to identify the first signal component, and thus also the timing of the first signal component in the sensor signal. In some embodiments, the first signal component can be identified using a thresholding algorithm (e.g. that identifies where in the sensor signal the amplitude of the signal exceeds a threshold), or a pattern matching or correlation algorithm that attempts to match a template 'touch' (as measured by a first sensor 48, 52; e.g. the sound of a touch or the movement of the touch screen 46 caused by a touch) to the windowed part of the sensor signal.

In some embodiments, the determined timing of the first signal component in the sensor signal can be used as the time at which the user touched the touch screen 46. Where timings of multiple touches are determined using the above method, these timings can be compared to each other and/or otherwise analysed to evaluate the touch inputs by the user (e.g. in a FTT).

In alternative embodiments, a signal processing delay relating to the first sensor 48, 52 can be determined (i.e. a delay in the processing from an analog sensor signal to a digital signal that can be processed by the processing unit 42) and this delay is used to 'correct' the timing of a detected first signal component in the first sensor signal to provide the determined touch time. As noted above, the signal processing delay may be known (e.g. determined during manufacture or calibration of the electronic device or other device comprising the first sensor 48, 52) or it can be estimated in embodiments where a stimulus is provided to the user and the stimulus can also be measured by the first sensor 48, 52). It will be appreciated that in this case, a stimulus may be used merely for determining the processing delay associated with the first sensor signal (e.g. by comparing an excitation signal to the sensor signal); i.e. the stimulus may not be used for prompting a user to press the touch screen.

Some embodiments of the step of using are described below with reference to FIG. 6.

In further embodiments, the method in FIG. 5 is used to determine the reaction time of a user to a stimulus (referred to as a 'first stimulus'), such as an audible sound, a light or a vibration. In these embodiments, the processing unit 42 also obtains an excitation signal that was used as an input to a transducer 50 to generate the first stimulus. As noted above, the transducer 50 may be a loudspeaker, a light source or a vibrating component. As with the touch signal and the sensor signal, the processing unit 42 may obtain the excitation signal by receiving the excitation signal in real time, oy by obtaining the excitation signal from the memory unit 44 or obtaining the excitation signal from another device or apparatus.

If the first sensor 48, 52 is sensitive to the first stimulus (i.e. the first sensor 48, 52 can sense the first stimulus, e.g. a microphone measuring a sound, or an accelerometer measuring a vibration), then as a result of the first stimulus, the sensor signal will include a second signal component corresponding to a measurement by the first sensor 48, 52 of the first stimulus. If the first sensor 48, 52 is not sensitive to the first stimulus (e.g. the first sensor is a microphone and the first stimulus is light), a second stimulus may be provided at the same time as the first stimulus that can be sensed by the first sensor 48, 52. In that case, the sensor signal from the first sensor will include a second signal component corresponding to a measurement of the second stimulus.

Step 105 then comprises using the excitation signal and the touch signal to identify the time window in the sensor signal that contains the first signal component and the second signal component. The windowed sensor signal is then used in step 107 to determine the timing of the second signal component.

The reaction time of the user to the first stimulus from the timing of the first signal component and the timing of the second signal component. In particular, the reaction time of the user can be determined as the difference between the timing of the first signal component and the timing of the second signal component. In some embodiments, the reaction time can also take into account any difference in the propagation time for the sound from the loudspeaker 50 (or headphones) to the user and for the sound from the loudspeaker 50 (or headphones) to the microphone 48.

A first exemplary embodiment of the processing in step 105 is described below with reference to FIG. 6. Although the exemplary embodiment is described with reference to an audible stimulus, a loudspeaker 50 and a microphone 48, it will be appreciated that the techniques can be applied to other types of stimulus and/or other types of transducer 50 and/or other types of sensor 48, 52.

Figure 6:
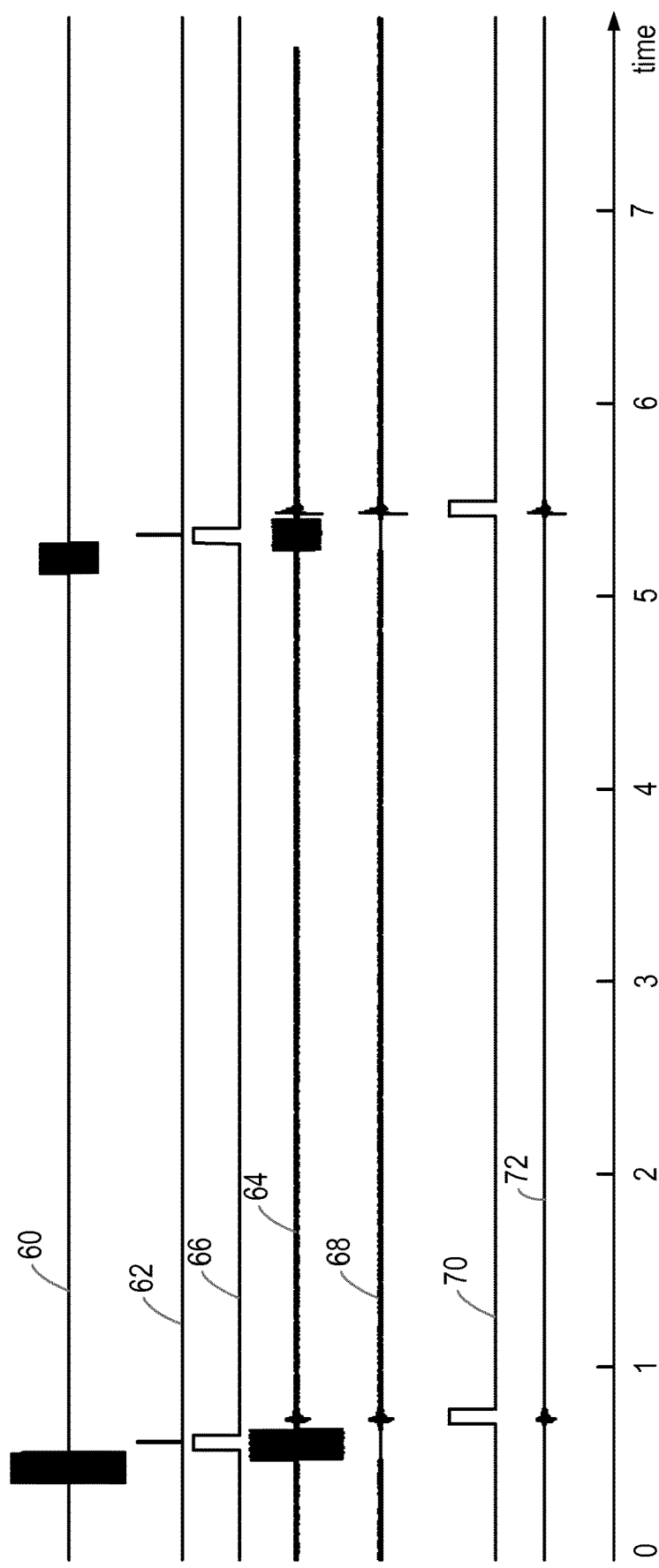
FIG. 6 is a graph illustrating the processing of the signals according to an embodiment.

Signal 60 in FIG. 6 is an exemplary (digital) excitation signal for a loudspeaker 50 or headphones that would cause the loudspeaker 50 or headphones to generate two audible stimuli (e.g. beeps) with different amplitudes. Signal 62 is an exemplary touch signal received from a touch screen 46 that shows two touches of the screen by the user in response to the audible stimulus. Signal 64 is an exemplary (digital) sensor signal received from a microphone 48 that includes the measured sound of the stimuli and touches of the touch screen 46. These signals can be processed as follows to determine the time at which the user touched the touch screen 46.

Firstly, a pulse train is generated from the touches detected in the touch screen signal 62. Each pulse in the pulse train (shown as signal 66 in FIG. 6) covers a detected touch in the touch signal 62, and can have a pulse width that approximately corresponds with the width of the touch as measured in the microphone signal. This width can be predetermined. The pulse train signal 66 therefore has an amplitude of 0 where it is not close to the timing of a touch of the screen 46, and an amplitude of 1 where it is close to the timing of a touch of the screen 46. Optionally, instead of a binary amplitude, a more gradual transition may be employed.

Next, the stimuli (i.e. beeps) are removed from the sensor (microphone) signal 64. This can be achieved by correlating the digital input sequence that went into the loudspeaker 50 (i.e. the excitation signal 60) with the digital output sequence 64 (the signal 64 output by the microphone 48). This correlation provides a delay between the stimulus and the second signal component (i.e. the stimulus as measured by the microphone 48). Using this delay, simply the stimuli (i.e. the second signal components) can be set to zero at the locations of the stimuli in the sensor signal 64. This results in the filtered signal 68 in FIG. 6. Alternatively an adaptive filter may be used to automatically subtract the stimuli from the sensor signal 64.

From filtered signal 68, a characteristic signal for the filtered sensor signal 68 is generated. The characteristic signal represents or corresponds to one or more characteristics of the filtered signal 68, such as the amplitude. In some embodiments, the characteristic signal is an envelope signal for the filtered signal 68. As a very coarse approximation, the envelope of the signal can be formed using the absolute value of the microphone signal 64. However, it will be appreciated that this is just a coarse approximation, and those skilled in the art will be aware of other ways in which an envelope of the microphone signal 64 can be generated. For example, an envelope may be constructed using a Hilbert transform. As another example, an envelope $e[n]$ may come from a sample to sample process, using a maximum follower:

$$e[n]=\alpha*e[n-1] \quad (9)$$

$$\text{if } abs(x[n])>e[n] \quad (10)$$

$$e[n]=abs(x[n]) \quad (11)$$

where the parameter $\alpha$ is a constant $0<\alpha<1$.

Next, the characteristic (e.g. envelope) signal and the pulse signal 66 are correlated to generate a delayed pulse signal 70. Correlating the pulse signal 66 with the characteristic signal provides a delay at which the timing of the touches of the touch screen 46 roughly correspond to the microphone representations of the touch screen touches, and this delay is applied to the pulse signal 66 to form the delayed pulse signal 70.

This delayed pulse train 70 is used to create a windowed microphone signal 64 (i.e. by multiplying the delayed pulse train 70 with the microphone signal 64). The time windowed microphone signal is shown as signal 72 in FIG. 6, and it can be seen that both the stimulus and the noise outside the windows have been removed, leaving (mainly) just the sound of the screen touches.

This windowed microphone signal 70 can be processed in step 107 to determine the timing of the first signal component in the sensor signal. In some embodiments, the first signal component can be identified using a thresholding algorithm (e.g. that identifies where in the sensor signal 72 the amplitude of the signal exceeds a threshold), or a pattern matching or correlation algorithm that attempts to match a template 'sound of a touch' to the sensor signal.

A second exemplary embodiment of the processing in step 105 is described below. The processing in this exemplary embodiment can be used when no stimulus is provided, and is similar to the above embodiment. Such an embodiment can be used for the FTT where the user is touching the screen without a stimulus prompt. Firstly, a pulse train is generated from the touches detected in the touch screen signal 62 as described above. Each pulse in the pulse train (shown as signal 66 in FIG. 6) covers a detected touch in the touch signal 62, and can have a pulse width that approximately corresponds with the width of the touch as measured in the microphone signal. The pulse train signal 66 therefore has an amplitude of 0 where it is not close to the timing of a touch of the screen 46, and an amplitude of 1 where it is close to the timing of a touch of the screen 46. Optionally, instead of a binary amplitude, a more gradual transition may be employed.

From the sensor (microphone) signal 64 a characteristic signal is generated. As above, the characteristic signal can be an envelope signal, which can be generated as described above, e.g. by forming the envelope of the signal using the absolute value of the microphone signal 64, using a Hilbert transform or using a maximum follower technique.

Next, the characteristic signal and the pulse signal 66 are correlated to generate a delayed pulse signal 70. Correlating the pulse signal 66 with the characteristic signal provides a delay at which the timing of the touches of the touch screen 46 roughly correspond to the microphone representations of the touch screen touches, and this delay is applied to the pulse signal 66 to form the delayed pulse signal 70.

This delayed pulse train 70 is used to create a windowed microphone signal 64 (i.e. by multiplying the delayed pulse train 70 with the microphone signal 64), which results in time windowed microphone signal 72 where the noise outside the windows has been removed, leaving (mainly) just the sound of the screen touches.

This windowed microphone signal 70 is then processed in step 107 to determine the timing of the first signal component in the sensor signal as described above.

As noted above, various different implementations of the apparatus 40 are possible, with different sensors 48, 50 and/or different transducers 50. Some specific examples are outlined below (although it will be appreciated that other implementations are possible).

In a first specific example, which can be used for a PVT, in addition to using the signal from a microphone 48, an accelerometer 52 can be used to measure the touches of the touch screen 46 by the user. The use of the accelerometer signal allows for improvements in the estimate of the delay time, which means that the accelerometer signal can be directly linked to the microphone signal.

In a second specific example, which can be used for a FFT, an auditory cue/stimulus (beep) could be used to indicate the start and optionally the end of the task.

In a third specific example, instead of using a microphone signal for a PVT, similar results for a FTT can be achieved by using an accelerometer signal. Since an audible stimulus will generally not be detected by the accelerometer, a second stimulus (e.g. a vibration) could be used at the same time as the audible stimulus that can be measured by the accelerometer. Alternatively, a gyroscope could be set up to be sensitive towards audible stimuli. However, for the FTT, the timings between consecutive finger taps are of interest, so this lack of a measurable stimulus in the accelerometer or gyroscope may not be a problem.

In examples where the user is provided with a visual stimulus (e.g. a flashing light) instead of an auditory stimulus, a second stimulus (e.g. a beep or vibration) at the same time as the light stimulus can be used that can be measured by the microphone or accelerometer respectively.

In the embodiments above it is assumed that the movement sensor (e.g. accelerometer and/or gyroscope) is in the same device as the touch screen 46. However, in alternative embodiments, the user may be wearing a smart watch (or other wearable device) that comprises one or more movement sensors, such as accelerometers, and therefore the signal from the smart watch may also be used to determine the timing of the touch of the touch screen 46 by the user. Furthermore, combining the measurements obtained at the arm, wrist or hand with the measurements made by the microphone and/or accelerometer in the electronic device may enable the motor skills of the user to be assessed (e.g.

it could be possible to determine how long it takes the user to touch the touch screen 46 from the initial movement of the arm/hand).

There is therefore provided a method and apparatus for improving the measurement of the timing of touches of a touch screen.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller. While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining a time at which a user touched a touch screen of an electronic device, the method comprising:
    obtaining a touch signal generated by the touch screen during a first time period, the touch signal indicating when the user touched the touch screen during the first time period;
    obtaining a sensor signal generated by a first sensor for at least the first time period, the sensor signal comprising a first signal component corresponding to a measurement by the first sensor of the user making contact with the touch screen;
    using the touch signal to identify a time window in the sensor signal containing the first signal component to generate a windowed sensor signal, wherein the obtained touch signal is used to identify a window of a predetermined width within the first time period, the predetermined width being shorter than the first time period and corresponding to a predetermined timing uncertainty for the touch signal; and
    processing the windowed sensor signal to determine the timing of the first signal component within the windowed sensor signal.

2. A method as claimed in claim 1, wherein the step of using comprises:
    generating a pulse signal from the touch signal, each pulse in the pulse signal corresponding to a detected touch in the touch signal;
    generating a characteristic signal for the sensor signal;
    correlating the pulse signal and the characteristic signal to generate a delayed pulse signal;
    using the delayed pulse signal to identify the time window in the sensor signal.

3. A method as claimed in claim 1, wherein the method further comprises:
    determining a signal processing delay relating to the first sensor; and
    determining the time at which the user touched the touch screen based on the determined timing of the first signal component and the determined signal processing delay.

4. A method as claimed in claim 1, wherein the method further comprises:
    obtaining an excitation signal used as an input to a first transducer to generate a first stimulus;
    wherein the sensor signal further comprises a second signal component corresponding to a measurement by the first sensor of the first stimulus or corresponding to a measurement by the first sensor of a second stimulus generated at the same time as the first stimulus;
    wherein the step of using comprises using the excitation signal and the touch signal to identify the time window in the sensor signal that contains the first signal component and the second signal component; and
    wherein the step of processing further comprises processing the windowed sensor signal to determine the timing of the second signal component.

5. A method as claimed in claim 4, wherein the method further comprises:
    generating the second stimulus using a second transducer at the same time that the first transducer generates the first stimulus, wherein the second stimulus is a different type of stimulus to the first stimulus.

6. A method as claimed in claim 4, wherein the method further comprises:
   determining the reaction time of the user to the first stimulus from the timing of the first signal component and the timing of the second signal component.

7. A method as claimed in claim 4, wherein the method further comprises:
   estimating the time taken for the first stimulus to travel from the first transducer to the user; and
   determining the reaction time of the user to the first stimulus from the timing of the first signal component, the timing of the second signal component and the estimate of the time taken.

8. A computer program product comprising a computer readable medium having computer readable code embodied therein, the computer readable code being configured such that, on execution by a suitable computer or processor, the computer or processor is caused to perform the method of claim 1.

9. An apparatus for determining a time at which a user touched a touch screen of an electronic device, the apparatus comprising:
   a processing unit configured to:
      obtain a touch signal generated by the touch screen during a first time period, the touch signal indicating when the user touched the touch screen during the first time period;
      obtain a sensor signal generated by a first sensor for at least the first time period, the sensor signal comprising a first signal component corresponding to a measurement by the first sensor of the user making contact with the touch screen;
      use the touch signal to identify a time window in the sensor signal containing the first signal component to generate a windowed sensor signal, wherein the obtained touch signal is used to identify a window of a predetermined width within the first time period, the predetermined width being shorter than the first time period and corresponding to a predetermined timing uncertainty for the touch signal; and
      process the windowed sensor signal to determine the timing of the first signal component within the windowed sensor signal.

10. An apparatus as claimed in claim 9, wherein the processing unit is configured to use the touch signal to identify a time window by:
   generating a pulse signal from the touch signal, each pulse in the pulse signal corresponding to a detected touch in the touch signal;
   generating a characteristic signal for the sensor signal;
   correlating the pulse signal and the characteristic signal to generate a delayed pulse signal;
   using the delayed pulse signal to identify the time window in the sensor signal.

11. An apparatus as claimed in claim 9, wherein the processing unit is further configured to:
   determine a signal processing delay relating to the first sensor; and
   determine the time at which the user touched the touch screen based on the determined timing of the first signal component and the determined signal processing delay.

12. An apparatus as claimed in claim 9, wherein the processing unit is further configured to:
   obtain an excitation signal used as an input to a first transducer to generate a first stimulus;
   wherein the sensor signal further comprises a second signal component corresponding to a measurement by the first sensor of the first stimulus or corresponding to a measurement by the first sensor of a second stimulus generated at the same time as the first stimulus; wherein the processing unit is configured to use the excitation signal and the touch signal to identify the time window in the sensor signal that contains the first signal component and the second signal component; and wherein the processing unit is further configured to process the windowed sensor signal by processing the windowed sensor signal to determine the timing of the second signal component.

13. An apparatus as claimed in claim 12, wherein the processing unit is further configured to:
   determine the reaction time of the user to the first stimulus from the timing of the first signal component and the timing of the second signal component.

14. An apparatus as claimed in claim 12, wherein the processing unit is further configured to:
   estimate the time taken for the first stimulus to travel from the first transducer to the user; and
   determine the reaction time of the user to the first stimulus from the timing of the first signal component, the timing of the second signal component and the estimate of the time taken.

15. An apparatus as claimed in claim 9, wherein the apparatus comprises the touch screen and the first sensor.

16. An apparatus for determining a time at which a user touched a touch screen of an electronic device, the apparatus comprising:
   a processing unit configured to:
   obtain a touch signal generated by the touch screen during a first time period, the touch signal indicating when the user touched the touch screen during the first time period;
   obtain a sensor signal generated by a first sensor for at least the first time period, the sensor signal comprising a first signal component corresponding to a measurement by the first sensor of the user making contact with the touch screen;
   use the touch signal to identify a time window in the sensor signal containing the first signal component to generate a windowed sensor signal, wherein the obtained touch signal is used to identify a window of a predetermined width within the first time period, the predetermined width being shorter than the first time period and corresponding to a predetermined timing uncertainty for the touch signal;
   process the windowed sensor signal to determine the timing of the first signal component within the windowed sensor signal;
   determine a signal processing delay based on a comparison of (i) the determined timing of the first signal component within the windowed sensor signal and (ii) the timing of the touch signal; and determine, using the determined signal processing delay, the time at which the user touched the touch screen.

* * * * *